United States Patent [19]

Wells

[11] Patent Number: 4,684,807

[45] Date of Patent: * Aug. 4, 1987

[54] FLOW CONTOURED ELECTRON CAPTURE DETECTOR CELL

[75] Inventor: Gregory J. Wells, Suisun, Calif.

[73] Assignee: Varian Associates, Inc., Palo Alto, Calif.

[*] Notice: The portion of the term of this patent subsequent to Mar. 17, 2004 has been disclaimed.

[21] Appl. No.: 733,854

[22] Filed: May 13, 1985

Related U.S. Application Data

[63] Continuation of Ser. No. 522,081, Aug. 11, 1983, abandoned.

[51] Int. Cl.[4] ............................................. G01N 27/66
[52] U.S. Cl. .................................... 250/381; 250/379; 324/465; 324/469; 422/89
[58] Field of Search ............................ 422/89, 90, 54; 436/153, 154; 250/435–438, 379, 381, 384, 389; 324/465, 469

[56] References Cited

U.S. PATENT DOCUMENTS

| | | | |
|---|---|---|---|
| 3,176,135 | 3/1965 | Lovelock | 250/379 |
| 3,361,907 | 1/1968 | Gregory | 250/389 |
| 3,372,000 | 3/1968 | Gallaway et al. | 422/54 |
| 4,063,156 | 12/1977 | Patterson | 324/465 |
| 4,264,817 | 4/1981 | Neukermans et al. | 324/465 X |

FOREIGN PATENT DOCUMENTS

| | | | |
|---|---|---|---|
| 2203767 | 8/1973 | Fed. Rep. of Germany | 422/54 |
| 1186525 | 4/1970 | United Kingdom . | |
| 1308598 | 2/1973 | United Kingdom | 422/54 |
| 0595670 | 3/1978 | U.S.S.R. | 422/54 |
| 0608089 | 5/1978 | U.S.S.R. | 324/469 |
| 0642650 | 1/1979 | U.S.S.R. | 422/89 |
| 0890224 | 12/1981 | U.S.S.R. | 422/54 |
| 0911301 | 3/1983 | U.S.S.R. | 250/381 |

OTHER PUBLICATIONS

Pulse-Modulated Electron Capture Detection with Nitrogen Carrier Gas, Patterson, J. of Chromatography, 134, 1977, pp. 25–37.
J of High Resolution Chromatography & Chromatography Comm. "A Micro-Volume Electron Capture Detector for Use in High..." G. Wells, pp. 651–654, 1983, vol. 6.
J of Chromatography, 235 (1982) 1–20, A. Neukermans, W. Kruger, D. McManigill "Non-Radioactive Electron-Capture Detector".
Anal. Chem 1980, 52, 473–482, "Improved Model of the Pulsed Electron Capture Detector" P. L. Gobby, E. P. Grimsrud and S. W. Warden.

Primary Examiner—Arnold Turk
Attorney, Agent, or Firm—Stanley Z. Cole; Gerald M. Fisher; David Schnapf

[57] ABSTRACT

A small volume electron capture detector has a cylindrical cell 120 inside which there is provided a generally funnel-shaped insert structure 130 having a cup-shaped section and a cylindrical section. The rims of the cup-shaped section nearly touch the inner walls of the cell 120 so as to separate the active volume from the areas at the top corners of the cell 120 which are not actively swept by the carrier gas, thus reducing the tailing of chromatographic peaks.

12 Claims, 4 Drawing Figures

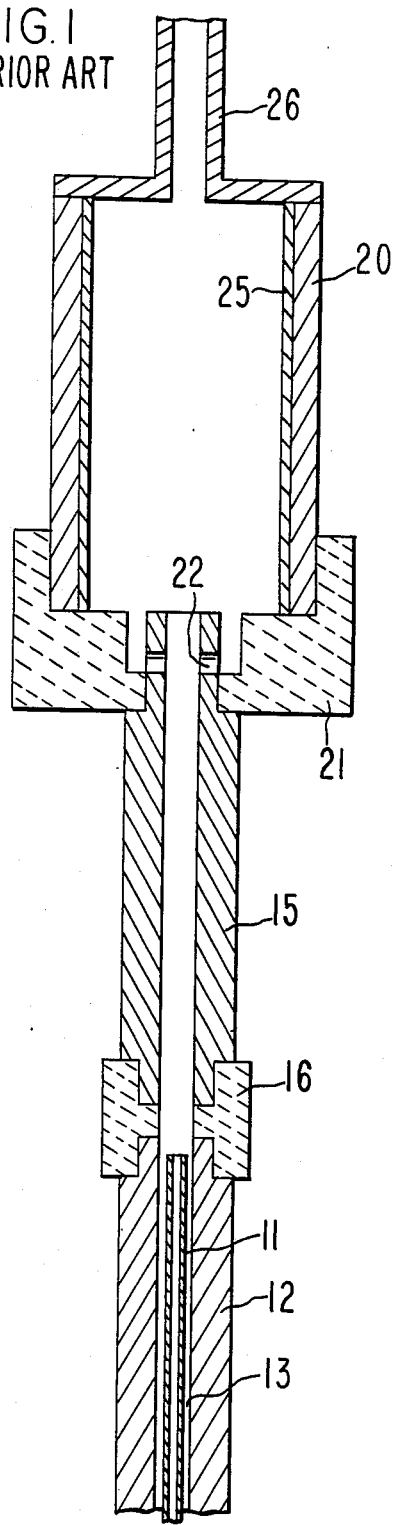
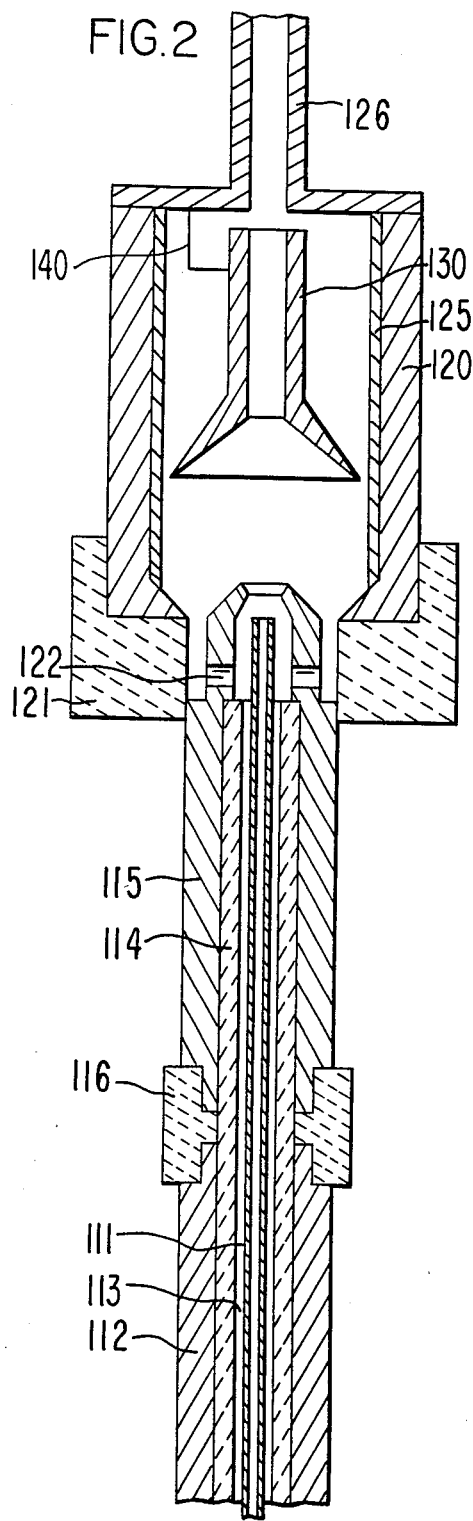

FLOW CONTOURED ELECTRON CAPTURE DETECTOR CELL

This application is a continuation of application Ser. No. 522,081, filed Aug. 11, 1983, now abandoned.

BACKGROUND OF THE INVENTION

This invention relates generally to a small volume electron capture detector cell and in particular to methods of minimizing or eliminating mixing effects in such a cell.

By the electron capture detection technique in the active volume of gas chromatography, a tritium or $Ni^{63}$ source ionizes the molecules of a carrier or make-up gas as it flows through the detector and the slow electrons thus produced are caused to migrate to the anode, forming a steady or pulsed current. This current becomes reduced if a sample containing electron absorbing molecules is introduced and this loss of current can be amplifed by an electrometer for analysis.

The electron capture detector is extremely sensitive to certain molecules such as alkyl halides, but is relatively insensitive to hydrocarbons, alcohols, ketones, etc. This selective sensitivity to halides makes the detection method especially valuable for the trace analysis of many environmentally important organic compounds, such as pesticides. Electron capture detectors, however, have not been used extensively in conjunction with high resolution capillary columns. They have often been considered to be too large in volume to be suitable for use with high resolution systems, and the detector cell generally contained regions not actively swept by the carrier gas. The latter phenomenon is sometimes called the mixing effects, or mixing volume effects, and such unswept regions are known to cause tailing of chromatographic peaks. The degree to which mixing occurs within the cell is dependent upon cell design and gas flow rate, this problem generally increasing as the length-to-diameter ratio (L/D) of the cell decreases.

It is therefore a general object of this invention to provide an electron capture detector suitable for high resolution analysis.

It is another object of the present invention to provide a small volume electron capture detector cell wherein the mixing volume effects are minimized or eliminated.

It is a further object of the present invention to provide an electron capture detector cell having an insert for eliminating the unswept regions therein.

SUMMARY OF THE INVENTION

The above and other objects are achieved by introducing into the electron capture detector cell a structure having a streamlined wall to define within the cell an active volume from which electrons are collected and to keep the unswept regions outside this active volume.

BRIEF DESCRIPTION OF THE DRAWINGS

FIG. 1 is a schematic cross-sectional view of a prior art electron capture detector.

FIG. 2 is a schematic cross-sectional view of an electron capture detector of the present invention.

DETAILED DESCRIPTION OF THE INVENTION

Figure 4:
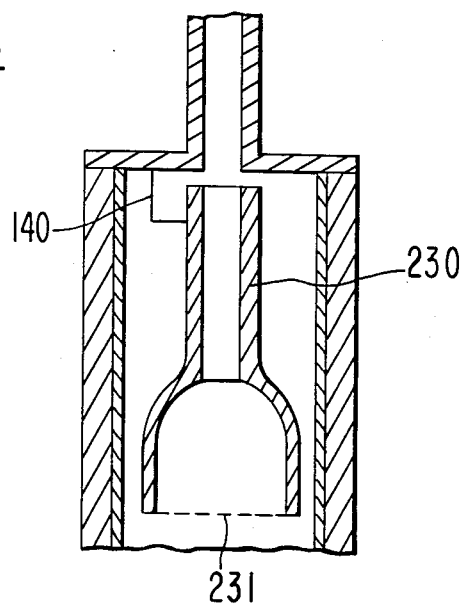
FIG. 4 is another embodiment of electron capture detector cell according to the present invention.

There is shown in FIG. 1 the general design of a prior art electron capture detection system (such as the commercially available one disclosed by P. L. Patterson in J. Chromatogr., 134 (1977) at page 25). The top portion of a gas chromatography column 11 through which the sample to be analyzed is led into the detector is housed concentrically inside an inlet tube 12 so as to form a passageway 13 having an annular cross section between the inner wall of the inlet tube 12 and the outer wall of the column 11. This passageway 13 is for a make-up gas, the use of which may become necessary, when a capillary column is used, in order to push the column gas (sample with a carrier gas) into the detector. The make-up gas then becomes mixed with the gas from the column 11. A generally cylindrical metal anode 15 is connected to the upper end of the inlet tube 12, separated therefrom by a ceramic insulator 16. The other end of the anode 15 opens into a cylindrical cell 20 (of length L and diameter D), separated therefrom by another ceramic insulator 21. The top end of the cylindrical anode 15 is provided with side ports 22. Thus, the sample from the column 11 and the make-up gas from the passageway 13 become mixed together as they travel upwards through the cylindrical anode 15, entering the interior of the cell 20 from below, some of this mixed gas passing through the side ports 22. On the inner wall of the cell 20 is a radioactive foil 25 which, for example, may be a $Ni^{63}$ or $H^3$ source. The top of the cell 20 is connected to an exit tube 26.

The prior art electron capture detector of FIG. 1 has several disadvantages. Firstly, because the sample from the column 11 is made to pass through the metal anode 15 before entering the detector cell 20, there results a sample loss by adsorption and this can cause chromatographic peak broadening. Secondly, a sample loss by adsorption occurs also on surfaces within the cell 20 especially when they are activated by hydrogen. Even when hydrogen is not used as the carrier gas, the presence of hot metal or ceramic surfaces with which the sample can come in contact should be expected to have detrimental effects. Thirdly, the make-up gas, when its use is necessary, tends to dilute the sample, decreasing the sensitivity of the detector. Fourthly, the detector cell 20, according to the prior art design as shown, includes regions at the top corners which are not actively swept by the carrier gas. An electron capture detector is generally sensitive to oxygen, and it is therefore necessary to prevent its back diffusion by increasing the length-to-diameter ratio of the exit tube 26. This necessarily tends to enlarge such unswept areas especially when the length-to-diameter ratio (L/D) of the cell 20 is decreased.

An electron capture detection system according to the present invention is shown in FIG. 2 wherein components which are identical or comparable to a component in FIG. 1 are given a three-digit numeral of which the last two are identical to those of the corresponding component in FIG. 1. In this embodiment, an insulating tube 114 of high purity alumina is positioned inside the inlet tube 112 and the anode 115 which are separated by a ceramic insulator 116. This insulating tube 114 extends up to a point just below the side ports 122 which are provided near the top of the anode 115. The gas chromatography column 111 through which the sample is led into the detector extends higher than in FIG. 1 and reaches beyond the side ports 122 so that only the make-up gas introduced through the annular passageway 113 between the outer wall of the column 111 and the inner wall of the insulating tube 114 will enter the detector cell through the side ports 122. These changes in the inlet system from FIG. 1 are intended to cause the make-up gas to sweep the sample only into the central region of the cell, minimizing the sample dilution by preventing the complete mixing with the make-up gas and reducing the contamination by the sample of the radioactive foil 125 which is disposed on the inner wall of the generally cylindrical cell 120. The top of the cell 120 is connected to an exit tube 126.

Placed inside the cell 120 is a metallic structure 130, the purpose of which is to limit the active volume of the detector 120, defined as the region from which electrons are collected for measurement, to below this structure 130, thereby separating the unswept areas from the active volume. For this purpose, this structure 130 is made of a conductive metal and maintained at the same potential as the side walls of the cell 120, or the radioactive foil 125, for example, by an electrical connection 140 to the latter. The structure 130 is generally shaped like a funnel, having a cylindrical section and a cup-shaped section. The cup-shaped section faces the top end of the column 111, while the cylindrical section which serves as a gas conduit, points upward to the exit tube 126. The cup-shaped section is so designed and positioned that its rims are closely adjacent to, but not completely touching, the radioactive foil 125 so that gas can pass through the gap therebetween, although a majority of the gas introduced into the detector cell 120 will be caused to pass through the cylindrical section of the structure 130. Thus, the top corners of the cell 120 which are not actively swept by the carrier gas, and hence previously referred to as the unswept areas, are effectively separated by the structure 130 from the region below which is approximately bounded by the inner surface of the cup-shaped section of the structure 130, a lower portion of the radioactive foil 125 and the top of the inlet system. The inner surface of the cup-shaped section may be tapered appropriately so as to streamline the gas flow through the center. With the insertion of this structure 130, therefore, mixing effects in the top corners of the cell 120 near the exit tube 126 are no longer of any significance because they do not occur within the active region.

Figure 3:
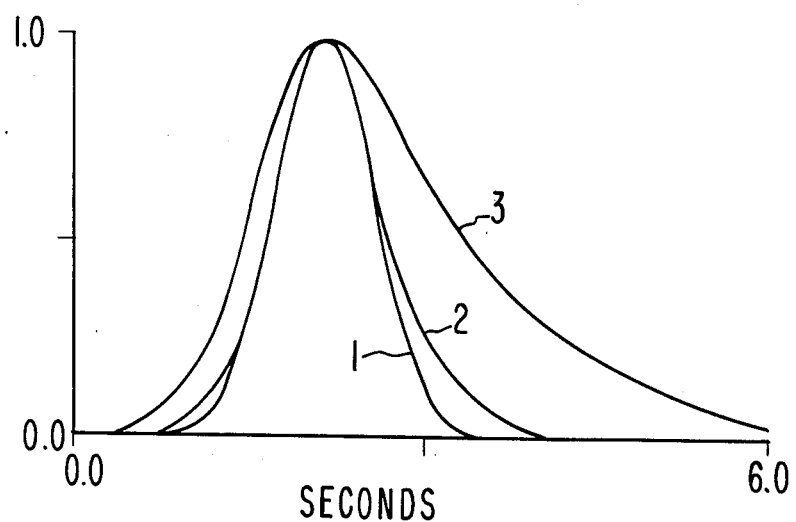
FIG. 3 is a comparison of measured response between electron capture detectors of FIGS. 1 and 2.

FIG. 3 shows the effect of inserting the structure 130 on the measured response. Curve 1 is for a flame ionization detector and is assumed to properly represent the actual input function to the detector. Curve 2 is for a 100-microliter electron capture detector of design according to FIG. 2, while Curve 3 is for a commercially available 350-microliter electron capture detector of prior art design according to FIG. 1. The flow rate for all three Curves is 10 milliliters/minute. The reduction in peak tailing in the case of Curve 2 is to be noted with respect to Curve 3.

FIG. 4 shows another design for the insert structure 230. In this design, the cup-shaped section is more cylindrical than conical as in FIG. 2 and there is provided a metal screen 231 at the lower end of the cup-shaped section to further serve to define the active region of the cell.

The present invention has been described above in terms of but a few embodiments. They, however, are intended to be illustrative rather than limiting and the disclosure is accordingly to be construed broadly. For example, the figures are to be understood only as being schematic so that they do not necessarily represent the true or intended dimensional relationships. The radioactive source may be placed differently and the design of the inlet system may be modified. Neither the use of a make-up gas nor a particular design of the inlet system is a requirement. The scope of the invention is limited only by the following claims.

What is claimed is:

1. An electron capture detector cell for use with a source of sample-bearing gas to be analyzed, and a source of make-up gas to aid in moving and isolating said sample-bearing gas, said cell comprising:
   a tubular body with a gas exit at one end;
   an anode at the other end of said tubular body;
   a radioactive source arranged about the inner surface of said tubular body;
   gas introduction means at said anode end of said tubular body for establishing an initial gas flow pattern within said tubular body in which sample-bearing gas is emitted centrally axially while being surrounded by a flow of axially-directed make-up gas moving toward said exit; and
   a structure made of electrically conductive material, located within said tubular body, electrically and physically defining an active region in said tubular body adjacent to said anode in which said sample-bearing gas is subject to bombardment of electrons from said radioactive source within said active region permitting detection of current variations as the constituents of said sample-bearing gas change; said structure inhibiting said flow of sample-bearing gas from contacting the walls of said tubular body while within said active region and for inhibiting recycling of gas from the portions of said tubular body not within said active region into said active region.

2. A cell as in claim 1 in which said structure is coaxial with said tubular body, is axially symmetric, is streamlined in contour, is spaced apart from said wall of said tubular body to allow a portion of said flow of make-up gas to flow between said wall and said structure, and is of low resistance to the downstream flow of gas, to readily allow flow toward said exit while inhibiting said recycling, and to streamline gas flow upstream of and through said structure.

3. A cell as in claim 2 in which said structure is funnel-shaped, having a tubular portion and a conical portion, and with the mouth of said conical portion directed toward said anode.

4. A cell as in claim 3 in which a gas permeable screen of electrically conductive material covers said mouth of said conical portion of said structure.

5. An electron capture detector cell for use with a source of sample gas to be analyzed, and a source of make-up gas, comprising:
   a tubular body with an entrance end and an exit end and defining a conductive inner wall;
   a conductive central axial electron collector anode at said entrance end, electrically isolated and spaced from said tubular body;
   nozzle means defined within said anode for introducing a flow of sample gas centrally within said cell, and for injecting a make-up gas about said sample gas, to move said sample gas along a central axial flow path;

said anode and body defining therebetween an elongated narrow annular channel coaxial with said anode, said make-up gas being released into said channel surrounding said sample gas and inhibiting said sample gas from contacting said inner wall;

control means comprising electrically conductive material in electrical contact with said inner wall within said body defining an active region adjacent to said anode and spaced from said nozzle means for inhibiting the mixing of gas from interior regions of said body downstream of said control means with gas in regions of said body upstream of said control means; and a radioactive source arranged about said inner wall and extending into said active region, said source ionizing said sample gas within said active region.

6. A cell as in claim 5 in which said nozzle has defined therein radially outwardly directed outlet means for said make-up gas.

7. A cell as in claim 5 in which said nozzle means further includes a first outlet located at the downstream end of said anode axially centrally, for releasing said sample gas, and a plurality of second outlets for said make-up gas, spaced axially donwnstream of and radially from said first outlet.

8. A cell as in claim 5 in which said control means comprises a funnel-shaped structure of electrically conductive material coaxial with said body, having a tubular portion oriented toward said exit end and a conical portion oriented toward said entrance end, and spaced apart from said conductive inner wall, said funnel-shaped structure in electrical contact with said conductive inner wall.

9. A cell as in claim 8 in which a gas permeable screen of electrically conductive material covers the mouth of said conical portion of said funnel-shaped structure.

10. An electron capture detector cell for use with a source of sample gas to be analyzed, and a source of make-up gas, comprising:

an enclosed tubular body having an entrance end and an exit, at least a portion of the tubular body being made of electrically conductive material;

a conductive central axial electron collector anode at said entrance end of said tubular body electrically insulated from said conductive portion of said tubular body;

nozzle means defined within said anode for introducing a flow of sample gas surrounded by a flow of make-up gas, within said tubular body;

a gas control structure within said tubular body having an inlet end oriented toward said nozzle and an outlet end, made of electrically conductive material, coaxially mounted within said tubular body, and in electrical contact with said electrically conductive portion of said tubular body for controlling the flow of gas and for defining an active region within said tubular body adjacent said anode;

a rim on said inlet end of said gas control structure, said rim being spaced away from the wall of said tubular body such that at least a portion of said flow of make-up gas flows through the space between said rim and said wall; and a radioactive source mounted on said wall of said tubular body, at least a portion of said radioactive source being within the active region of said cell.

11. A cell as in claim 10 in which said gas control structure is funnel-shaped having a tubular portion comprising said outlet end and a conical portion comprising said inlet end.

12. A cell as in claim 11 in which a gas permeable screen of electrically conductive material covers said inlet end of said gas control structure.

* * * * *